US008725427B2

(12) United States Patent
Won

(10) Patent No.: US 8,725,427 B2
(45) Date of Patent: May 13, 2014

(54) METHOD AND APPARATUS FOR ESTIMATING FEATURES OF TARGET MATERIALS BY USING KINETIC CHANGE INFORMATION

(76) Inventor: Yong Gwan Won, Gwangju (KR)

(*) Notice: Subject to any disclaimer, the term of this patent is extended or adjusted under 35 U.S.C. 154(b) by 479 days.

(21) Appl. No.: 12/863,985

(22) PCT Filed: Jan. 21, 2009

(86) PCT No.: PCT/KR2009/000308
§ 371 (c)(1),
(2), (4) Date: Jul. 21, 2010

(87) PCT Pub. No.: WO2009/093840
PCT Pub. Date: Jul. 30, 2009

(65) Prior Publication Data
US 2010/0292932 A1 Nov. 18, 2010

(30) Foreign Application Priority Data

Jan. 22, 2008 (KR) .................. 10-2008-0006627
Dec. 30, 2008 (KR) .................. 10-2008-0137468

(51) Int. Cl.
*G01N 33/48* (2006.01)

(52) U.S. Cl.
USPC ................. 702/22; 702/33; 436/95

(58) Field of Classification Search
USPC ....................... 702/33, 22; 436/95
See application file for complete search history.

(56) References Cited

U.S. PATENT DOCUMENTS 7,018,843 B2   3/2006  Heller
2003/0023152 A1*  1/2003  Abbink et al. ............. 600/316
2003/0096420 A1*  5/2003  Heller ......................... 436/63
2003/0211625 A1* 11/2003  Cohan et al. ................ 436/95
2006/0281985 A1* 12/2006  Ward et al. .................. 600/365

FOREIGN PATENT DOCUMENTS

KR   10-2006-0019442 A   3/2006
KR   10-2007-0027527 A   3/2007

OTHER PUBLICATIONS

Hieu Trung Huyng, Jung-Ja Kim and Yonggwan Won, "Non-Linear Estimation Methods for Hematocrit Density based on Changing Pattern of Transduced Anodic Current Curve", WSEAS Transactions on Information Science and Applications, Nov. 1, 2008, pp. 1541-1550, vol. 5/No. 11.
Junseok Park, Hieu Trung Huynh, and Yonggwan Won, "Support Vector Machine for Hematocrit Density Estimation based on Changing Patterns of Transduced Anodic Current", Proc. of the 2008 Intl. Conf. on Convergence and Hybrid Information Technology, Nov. 11, 2008, pp. 459-460, Busan, South Korea.
Hieu Trung Huynh, Jung-Ja Kim, and Yonggwan Won, "Comparison of Nonlinear Methods for Hematocrit Estimation from the Transduced Anodic Current Curve", Proc. of Mathematical Methods, Computational Techniques, Non-linear Systems, Intelligent Systems, Oct. 26, 2008, pp. 156-161, Corf, Greece.

(Continued)

*Primary Examiner* — John Breene
*Assistant Examiner* — Haihui Zhang
(74) *Attorney, Agent, or Firm* — John K. Park; Park Law Firm

(57) ABSTRACT

Disclosed are a method and an apparatus for estimating the features (concentration, weight, volume, etc.) of target materials, by using kinetic change information along time, when measuring the results of a chemical reaction between two materials, target materials and reactant, with an optical or electrochemical method.

20 Claims, 11 Drawing Sheets

(56) References Cited

OTHER PUBLICATIONS

Hieu Trung Huynh and Yonggwan Won, "Hematocrit Estimation from Transduced Current Patterns Using Single Hidden Layer Feedforward Neural Networks", Proc. of the 2007 International Conference on Convergence Information Technology, Nov. 21, 2007, pp. 1384-1388.

Hieu Trung Huynh and Yonggwan Won, "Neural Networks for Estimation of Hematocrit Density from Transduced Current Curve Patterns", Proc. of 2008 IEEE International Conference on Networking, Sensing and Control, Apr. 6, 2008, pp. 1384-1388.

Hieu Trung Huynh and Yonggwan Won, "Henatocrit Estimation from Compact Single Hidden Layer Feedforward Neural Networks Trained by Evolutionary Algorithm", 2008 IEEE World Congress on Computational Intelligence, Jun. 1, 2008, pp. 2967-2971, Hong Kong.

Hieu Trung Huynh and Yonggwan Won, "The Use of Evolutionary Algorithm in Training Neural Networks for Hematocrit Estimation", Evoluntinoary Computation, Dec. 2009, In-Tech.

* cited by examiner

Fig. 4

| TRUE MEASURED VALUE(T) | FEATURE VALUE (M) | MEASURED VALUE (C) OF COMMERCIAL DEVICE | ME | CE |
|---|---|---|---|---|
| 50.40 | 53.55 | 41.00 | 9.92 | 88.36 |
| 50.40 | 56.21 | 53.00 | 33.73 | 6.76 |
| 58.20 | 68.92 | 61.00 | 114.97 | 7.84 |
| 58.40 | 60.18 | 60.00 | 67.52 | 2.56 |
| 59.10 | 67.29 | 73.00 | 67.13 | 193.21 |
| 60.60 | 70.67 | 61.00 | 101.44 | 0.16 |
| 61.70 | 56.95 | 67.00 | 22.58 | 28.09 |
| 62.50 | 71.39 | 64.00 | 78.97 | 2.25 |
| 67.80 | 67.26 | 70.00 | 0.29 | 4.84 |
| 69.50 | 65.13 | 68.00 | 19.13 | 2.25 |
| 69.60 | 69.79 | 64.00 | 0.04 | 31.36 |
| 69.80 | 80.08 | 77.00 | 105.58 | 51.84 |
| 69.90 | 82.36 | 70.00 | 56.79 | 0.01 |
| 72.40 | 81.09 | 73.00 | 75.53 | 0.36 |
| 73.40 | 80.35 | 68.00 | 48.25 | 29.16 |
| 73.50 | 85.32 | 80.00 | 139.61 | 42.25 |
| 75.70 | 79.71 | 68.00 | 16.11 | 59.29 |
| 76.00 | 86.34 | 71.00 | 106.83 | 25.00 |
| 76.10 | 83.51 | 75.00 | 54.98 | 1.21 |
| 78.40 | 76.65 | 83.00 | 3.06 | 21.16 |
| 80.90 | 75.54 | 77.00 | 28.70 | 15.21 |
| 81.10 | 86.00 | 81.00 | 24.03 | 0.01 |
| 82.30 | 81.35 | 84.00 | 0.90 | 2.89 |
| 83.90 | 81.95 | 88.00 | 3.80 | 16.81 |
| 86.20 | 80.92 | 80.00 | 27.89 | 38.44 |
| 87.00 | 92.09 | 84.00 | 25.94 | 9.00 |
| 89.50 | 90.16 | 92.00 | 0.43 | 6.25 |
| 91.80 | 87.52 | 93.00 | 18.31 | 1.44 |
| 93.60 | 88.58 | 91.00 | 25.21 | 6.76 |
| 93.80 | 100.97 | 94.00 | 51.35 | 0.04 |
| 94.10 | 96.49 | 94.00 | 5.73 | 0.01 |
| 96.60 | 92.36 | 102.00 | 18.00 | 29.16 |
| 98.10 | 98.26 | 103.00 | 0.02 | 24.01 |
| 98.60 | 104.82 | 106.00 | 38.72 | 54.76 |
| 98.70 | 110.29 | 93.00 | 134.42 | 32.49 |
| 99.80 | 103.64 | 96.00 | 14.72 | 14.44 |
| 100.00 | 104.60 | 107.00 | 21.14 | 49.00 |
| 100.00 | 106.64 | 107.00 | 44.10 | 49.00 |
| 101.00 | 110.85 | 108.00 | 96.93 | 49.00 |
| 101.00 | 112.35 | 120.00 | 128.84 | 361.00 |
| 102.00 | 105.32 | 109.00 | 11.08 | 49.00 |
| 103.00 | 107.80 | 99.00 | 23.02 | 16.00 |
| 103.00 | 103.19 | 105.00 | 33.86 | 16.00 |
| 110.00 | 100.55 | 112.00 | 89.23 | 4.00 |
| 111.00 | 104.11 | 110.00 | 47.46 | 1.00 |
| 111.00 | 107.87 | 130.00 | 9.82 | 361.00 |
| 115.00 | 133.33 | 127.00 | 336.16 | 144.00 |
| 116.00 | 124.73 | 128.00 | 76.14 | 144.00 |
| 118.00 | 103.88 | 111.00 | 199.33 | 49.00 |
| 118.00 | 117.40 | 114.00 | 0.36 | 16.00 |
| 119.00 | 126.21 | 132.00 | 51.91 | 169.00 |

TABLE CONTINUES

| | | | | |
|---|---|---|---|---|
| 120.00 | 126.42 | 108.00 | 41.16 | 144.00 |
| 122.00 | 126.10 | 123.00 | 16.79 | 1.00 |
| 125.00 | 132.36 | 131.00 | 54.20 | 36.00 |
| 126.00 | 123.10 | 127.00 | 8.44 | 1.00 |
| 127.00 | 120.38 | 125.00 | 43.83 | 4.00 |
| 131.00 | 132.40 | 136.00 | 1.96 | 25.00 |
| 137.00 | 138.28 | 155.00 | 1.63 | 324.00 |
| 139.00 | 134.42 | 148.00 | 21.01 | 81.00 |
| 145.00 | 139.66 | 142.00 | 28.52 | 9.00 |
| 146.00 | 144.94 | 136.00 | 1.11 | 100.00 |
| 147.00 | 155.32 | 170.00 | 69.17 | 529.00 |
| 149.00 | 135.91 | 155.00 | 171.37 | 36.00 |
| 150.00 | 149.85 | 174.00 | 0.02 | 576.00 |
| 151.00 | 160.40 | 136.00 | 88.34 | 225.00 |
| 154.00 | 168.87 | 170.00 | 221.23 | 256.00 |
| 155.00 | 150.48 | 155.00 | 20.48 | 0.00 |
| 157.00 | 168.64 | 166.00 | 135.43 | 81.00 |
| 161.00 | 167.02 | 171.00 | 36.26 | 100.00 |
| 161.00 | 169.07 | 150.00 | 65.09 | 121.00 |
| 165.00 | 178.27 | 194.00 | 176.01 | 841.00 |
| 166.00 | 181.94 | 190.00 | 254.10 | 576.00 |
| 167.00 | 161.44 | 186.00 | 30.93 | 361.00 |
| 169.00 | 158.92 | 166.00 | 101.54 | 9.00 |
| 169.00 | 173.14 | 181.00 | 17.15 | 144.00 |
| 170.00 | 172.23 | 193.00 | 4.99 | 529.00 |
| 177.00 | 176.07 | 177.00 | 0.86 | 0.00 |
| 179.00 | 179.38 | 202.00 | 0.15 | 529.00 |
| 183.00 | 194.90 | 186.00 | 141.66 | 9.00 |
| 197.00 | 190.50 | 218.00 | 42.24 | 441.00 |
| 197.00 | 211.78 | 218.00 | 218.56 | 441.00 |
| 198.00 | 210.86 | 218.00 | 165.34 | 400.00 |
| 209.00 | 194.11 | 206.00 | 221.64 | 9.00 |
| 212.00 | 217.18 | 213.00 | 26.82 | 1.00 |
| 221.00 | 209.07 | 244.00 | 142.22 | 529.00 |
| 236.00 | 229.43 | 254.00 | 43.15 | 324.00 |
| 242.00 | 227.83 | 254.00 | 200.73 | 144.00 |
| 246.00 | 227.00 | 242.00 | 361.13 | 16.00 |
| 252.00 | 245.07 | 254.00 | 48.08 | 4.00 |
| 254.00 | 263.90 | 278.00 | 97.93 | 576.00 |
| 256.00 | 254.28 | 280.00 | 2.95 | 576.00 |
| 260.00 | 240.07 | 272.00 | 397.07 | 144.00 |
| 262.00 | 259.21 | 271.00 | 7.77 | 81.00 |
| 276.00 | 277.96 | 302.00 | 3.85 | 676.00 |
| 292.00 | 286.07 | 304.00 | 35.18 | 144.00 |
| 294.00 | 284.66 | 317.00 | 87.15 | 529.00 |
| 339.00 | 315.77 | 342.00 | 539.56 | 9.00 |
| 342.00 | 354.68 | 370.00 | 160.70 | 784.00 |
| 381.00 | 352.95 | 361.00 | 786.86 | 400.00 |
| 384.00 | 400.60 | 402.00 | 275.72 | 324.00 |
| | | RMSE | 9.13 | 12.05 |

ERROR = MEASURED VALUE − ACCURATE VALUE
(D = M − T)

Fig. 10

| SAMPLE | HEMATOCRIT | YSI 2300 | ESTIMATED HEMATOCRIT | | ESTIMATED BLOOD GLUCOSE | | BLOOD GLUCOSE BY COMMERCIAL PRODUCT | |
|---|---|---|---|---|---|---|---|---|
| | | | VALUE | ERROR | VALUE | ERROR | VALUE | ERROR |
| 1 | 25.8 | 142 | 26.35786 | -0.55786 | 135.3742 | 6.625786 | 149 | -7 |
| 2 | 25.6 | 73.5 | 26.01793 | -0.41793 | 66.1883 | 7.311696 | 80 | -6.5 |
| 3 | 27.9 | 78 | 42.17428 | -14.2743 | 75.02421 | 2.975789 | 80 | -2 |
| 4 | 29.8 | 100 | 31.07102 | -1.27102 | 95.95184 | 4.048159 | 107 | -7 |
| 5 | 27 | 101 | 20.2388 | 6.761203 | 103.0277 | -2.0277 | 120 | -19 |
| 6 | 23.5 | 106 | 34.91512 | -11.4151 | 107.0542 | -1.05418 | 116 | -10 |
| 7 | 25.7 | 166 | 28.69188 | -2.99188 | 177.6507 | -11.6507 | 190 | -24 |
| 8 | 27.2 | 167 | 27.77893 | -0.57893 | 173.1514 | -6.1514 | 186 | -19 |
| 9 | 25.7 | 170 | 35.13961 | -9.43961 | 184.177 | -14.177 | 193 | -23 |
| 10 | 39.4 | 37.1 | 42.73437 | -3.33437 | 32.33052 | 4.769476 | 37 | 0.1 |
| 11 | 33.3 | 41.3 | 33.6994 | -0.3994 | 36.3893 | 4.910699 | 46 | -4.7 |
| 12 | 32.6 | 61.7 | 34.1175 | -1.5175 | 57.61796 | 4.082037 | 67 | -5.3 |
| 13 | 39.2 | 102 | 41.14992 | -1.94992 | 108.464 | -6.46399 | 114 | -12 |
| 14 | 32.8 | 110 | 42.47456 | -9.67456 | 107.1884 | 2.811562 | 112 | -2 |
| 15 | 39.6 | 111 | 41.5258 | -1.9258 | 116.6896 | -5.66956 | 122 | -11 |
| 16 | 34.7 | 247 | 37.28243 | -2.58243 | 251.3489 | -4.34886 | 259 | -12 |
| 17 | 31.9 | 122 | 27.07687 | 4.823132 | 115.7674 | 6.232561 | 129 | -7 |
| 18 | 39 | 252 | 34.08951 | 4.910494 | 244.6027 | 7.397349 | 254 | -2 |
| 19 | 42.1 | 46.7 | 43.71047 | -1.61047 | 47.86436 | -1.16436 | 52 | -5.3 |
| 20 | 43.8 | 58.4 | 43.25978 | 0.540223 | 55.61787 | 2.782128 | 60 | -1.6 |
| 21 | 44.3 | 69.8 | 42.66408 | 1.635924 | 72.29208 | -2.49208 | 77 | -7.2 |
| 22 | 43 | 102 | 41.86669 | 1.133314 | 103.856 | -1.85599 | 109 | -7 |
| 23 | 45.2 | 103 | 47.32182 | -2.12182 | 96.8394 | 6.160597 | 99 | 4 |
| 24 | 42.2 | 119 | 41.94366 | 0.25634 | 116.8981 | 2.101912 | 122 | -3 |
| 25 | 42.4 | 260 | 31.77023 | 10.62977 | 261.3342 | -1.33424 | 272 | -12 |
| 26 | 45.7 | 263 | 47.62314 | -1.92314 | 246.0042 | 16.9958 | 248 | 15 |
| 27 | 41.9 | 292 | 40.61763 | 1.282367 | 298.1729 | -6.17288 | 304 | -12 |
| | | | | RMSE | 5.324757 | RMSE | | 8.91481 |

(a)

(b)

METHOD AND APPARATUS FOR ESTIMATING FEATURES OF TARGET MATERIALS BY USING KINETIC CHANGE INFORMATION

TECHNICAL FIELD

The present invention relates to a method and apparatus which, at the time of optically or electrochemically measuring the results of a chemical reaction of one chemical material (a measurement target material) with another chemical material (a reactant), acquires a correlation between kinetic change information which indicates the results of a chemical reaction varying with the passage of time and the feature values (concentration, weight, amount, etc.) of the measurement target material in advance from a large number of samples that can be statistically accommodated, and then estimates and calculates the feature values of the measurement target material using both kinetic change information, obtained when a new sample is provided, and the correlation obtained in advance.

Further, the present invention relates, in general, to an error correction method and apparatus using kinetic change information obtained at the time of optically or electrochemically measuring the results of a chemical reaction, and, more particularly, to an error correction method and apparatus, which corrects the feature values of a first material using kinetic change information about the feature values of the first material, a correction between the kinetic change information and the feature values of a second material, and a correlation between the feature values of the second material and the measurement errors of the first material.

BACKGROUND ART

When measuring the amount of the target material from the sample of mixture of a large number of chemical substances by either optical or electrochemical method, the result of chemical reaction between the target material and the corresponding material (chemically reacting material) is measured. When one or more other substances causing interference with a procedure for measuring the target material are unfortunately present in a mixture sample, obstruction attributable to such an interfering substance is caused.

Such an obstruction attributable to the interfering substances causes measurement errors to take place with respect to the target material, and thus becomes the principal cause of deteriorating the performance and reliability of products. In order to overcome this deterioration, conventional methods have concentrated their energy on the use of a scheme of previously eliminating interfering substances using chemical processing or a scheme of separately measuring independent values with which remove the effect of interference afterward. These methods are problematic in that the overall measurement process is complicated due to the addition of a chemical processing procedure or a separate measurement procedure, thus requiring high cost, and in that errors that may occur in the separate measurement procedure are accumulated, thus deteriorating accuracy.

That is, most conventional technologies have placed emphasis on the elimination of measurement errors via improvement based on an additional chemical procedure during the measurement process. Such technology is problematic in that qualitative improvement of various types of materials related to the measurement process is required, or a process for eliminating measurement errors is complicated by intending to reduce errors via a multi-step reaction procedure, and in that a process for manufacturing products which follow the above process is complicated, thus increasing the costs of products.

As one conventional technology, Korean Pat. Appln. No. 1989-0014308 (filed on Oct. 5, 1989) discloses "measurement error compensation method and light source control method for a blood glucose meter".

The conventional technology discloses a measurement error detection routine which emits light to a non-discolored blood sugar test paper required and detects a measurement error using reflected light to measure blood sugar concentration, and a measurement error compensation method for a blood glucose meter which compensates for measurement errors by calculating the value of the light, reflected from the blood sugar test paper discolored according to the blood sugar concentration, and the measurement errors detected by the measurement error detection routine. However, there is a problem because separate measurement errors must be detected in real time using the measurement error detection routine for the purpose of error correction, thus complicating a manufacturing process. Further, the conventional technology does not disclose a method of estimating the feature values of a measurement target material using the temporal change of measured values. Furthermore, the conventional technology is aimed at reducing errors which occur due to the differences between the colors of blood sugar test paper.

As another conventional technology, Korean Pat. Appln. No. 2006-0025890 (filed on Mar. 21, 2006) discloses "test strip for electrochemical biosensors capable of effectively compensating for hematocrit interference."

The above technology provides a scheme for compensating for existing signal decrement using an electrical signal obtained from the internal material of a red blood cell, which determines hematocrit. In this scheme, a separate electrode is configured, and blood cell interference corrective for reacting with blood cells within a physiological sample and generating charges corresponding to the concentration of the blood cells are included, thus compensating for the existing signal decrement using the electrical signal obtained from the internal material of the red blood cells. However, this technology accompanies complication in a manufacturing and measurement process due to a complicated electrode structure and the provision of separate supplements, and does not disclose the estimation and calculation of the feature values of a measurement target material using the temporal change characteristics of measured values.

As a further conventional technology, U.S. Pat. Nos. 5,708,247 and 5,951,836 (entitled "Disposable Glucose Test Strips, And Methods And Compositions For Making Same) and U.S. Pat. No. 6,241,862 (entitled "Disposable Test Strips With Integrated Reagent/Blood Separation Layer") disclose a technology for applying a nonconductive material to an electrode system to reduce interference effects on hematocrit, wherein both a method of manufacturing a carbon paste electrode system using screen printing technology and a reagent/blood separation layer fixed onto the surface of the electrode system are described. This conventional technology also includes the structure of the electrode and the application of a separate material, and does not include a technology for estimating and calculating the feature values of a measurement target material based on kinetic change indicating the temporal change of measured values.

Among conventional technologies, as a commercialized product using a thin film-type electrochemical enzymatic electrode, there is YSI 2300 STAT PLUS (Yellow Spring Instrument, Inc.). This technology is characterized in that three types of electrodes, that is, an enzymatic thin film, an external thin film, and an internal thin film, and in that an enzymatic material reacting with an analyte is manufactured as a thin film, and functional macromolecular thin films are manufactured and combined with each other on the inside and outside of the enzymatic thin film, thus effectively preventing red blood cells, protein, etc. from being adsorbed on the surfaces of the electrodes. The thin film-type enzymatic electrode can innovatively eliminate hematocrit interference, but the application of three types of thin films to the electrode system is accompanied by a complicated manufacturing process and high cost, thus increasing blood consumption and lengthening the reaction response time. This conventional technology is also intended to reduce errors using the enzymatic electrode and does not include a technology for estimating and calculating the feature values of a measurement target material based on the kinetic change of the measurement target material.

As conventional technology, Korean Pat. Appln. No. 2006-7003547 (entitled "electrochemical feature analysis method and apparatus" filed on Feb. 21, 2006) discloses a technology for correcting an analyte-dependent signal using analyte-independent signal information so as to more accurately evaluate an analyte, wherein the analyte-dependent signal which is not corrected is corrected based on observed analyte-independent voltage attenuation, and then a corrected analyte-dependent signal is formed. Voltage or current sufficient to cause the oxidation or reduction of an analyte or a medium is produced between two cell electrodes, and a slope in the chemical voltage of the analyte or the medium between the two electrodes is formed by the voltage or current. After the slope has been formed, the analyte-independent signal is obtained from the relaxation of the chemical voltage slope occurring when the applied voltage or current is stopped, and this analyte-independent signal is used to correct analyte-dependent signals obtained during the application of the voltage or current. This conventional technology is intended to perform correction using the signals obtained with the voltage supplied and without the voltage supplied, and does not include a technology for estimating and calculating feature values using kinetic change information obtained with the voltage supplied.

As conventional technology, Korean Pat. Appln. No. 2003-0036804 (entitled "electrochemical biosensor" filed on Jun. 9, 2003) relates to a sensitive layer composite capable of reducing measurement errors corresponding to the amount of hematocrit by decreasing a dependent tendency attributable to the hematocrit difference of blood, and a biosensor including the sensitive layer composite, wherein a technology for reducing errors attributable to an interfering substance using a chemical processing method added to the biosensor is disclosed. However, this does not include a technology for estimating and calculating feature values using kinetic change indicating the temporal change of values measured on a measurement target material.

DISCLOSURE

Technical Problem

The present inventors have developed a method of estimating and calculating the feature values of a target material to be measured based on kinetic change indicating the results of chemical reaction along the passage of the time, rather than methods including factors of increasing cost, such as by adding a complicated chemical procedure or changing a structure to eliminate the influence of a specific interfering substance, as a result of making efforts and doing research so as to estimate the feature values of the target material to be measured so that the feature values are approximate to accurate measured values, thus completing the present invention.

Accordingly, an object of the present invention is to provide a method and apparatus for estimating and calculating the feature values of a measurement target material using a signal processing scheme for the kinetic change signal of the measurement target material, without using a scheme which exploits separate complicated chemical processing for reducing measurement errors via the pre-elimination of an interfering substance and any special structure required for such complicated chemical processing.

Another object of the present invention is to provide a simple and very efficient method and apparatus, which acquires only a kinetic change signal while maintaining an existing measurement procedure and structure without additional measurement procedure or special structure in the measurement device so as to eliminate measurement errors attributable to an interfering substance, and thereafter estimates and calculates the feature values of a measurement target material using both kinetic change information and a correlation function, which are both obtained from a large number of samples that can be statistically accommodated; the correlation function has been previously determined with regard to the relationships between the kinetic changing information and the true value measured by approved reference machine.

A further object of the present invention is to provide a method and apparatus for reducing errors from the measured values of a target material by the post-processing for compensation of error caused by the influence of an interfering substance using signal processing method on the kinetic signal obtained from the sample to be measured, without using a scheme which exploits separate complicated chemical processing for reducing measurement errors via the previous elimination of an interfering substance and any special structure in the measurement device required for such complicated chemical processing.

Yet another object of the present invention is to provide a simple and very efficient error correction method and apparatus, which acquires only a kinetic change signal while maintaining an existing measurement procedure and structure without additional measurement procedure and special structure in entire manufacturing process for eliminating errors, and thereafter eliminates errors from the measured values of the target material using previously determined correlation function with the kinetic change information.

The objects of the present invention are not limited to the above-described objects and other objects that are not described will be apparently understood by those skilled in the art from the following description.

Technical Solution

In order to accomplish the above objects, the present invention provides a method of estimating feature values of a measurement target material using kinetic change information, comprising acquiring kinetic change information; and estimating and calculating feature values of the measurement target material using both the kinetic change information and a previously determined correlation function. In this case, the kinetic change information denotes a change in the feature values of the measurement target material over time, that is, a change in a chemical reaction between the measurement target material and a reactant over time.

In a preferred embodiment, the correlation function denotes an optimal correlation between true measured values of the measurement target material and the kinetic change information, and can be obtained using a mathematical, logical or statistical method or an artificial intelligence method, etc. The true measured value for the measurement target material is measured for a plurality of samples in an environment in which interference is eliminated, and the kinetic change information is a pattern of kinetic change over time also obtained from a large number of samples that can be statistically accommodated.

In a preferred embodiment, the correlation function minimizes a mean error (Root-Mean-Squared-Error: RMSE) $E_g$ defined in the following Equation 1 for a large number of samples:

$$E_g = \sqrt{\frac{\sum_{i=1}^{n}(T(i) - M(i))^2}{n}} \quad <\text{Equation 1}>$$

where n is a total number of samples, i is an index indicating each sample, T(i) is a true measured value of the measurement target material, and M(i) is a feature value of the measurement target material estimated based on kinetic change using the correlation function, wherein $E_g$ denotes a mean error of a total of n samples. Therefore, as the estimated values M(i) or all samples are closer to the true measured values T(i), RMS error $E_g$ becomes smaller. With respect to given n samples, when an optimal correlation is obtained, the RMS error is minimized. The true measured values denote values obtained by a separate accurate measuring device or typically authorized/approved reference equipment.

In a preferred embodiment, the measurement target material may be glucose (blood sugar) in blood. In this case, the feature value is the glucose concentration in the blood and the kinetic change information may be information in which a measured value of glucose concentration changes over time, that is, information in which an electrical signal appearing as a result of a reaction of glucose in blood with a reactant (for example, glucose oxidase enzyme), which is prepared on a biosensor for blood sugar measurement and reacts with glucose, changes with the passage of time.

As an example of a method of estimating the feature values of the measurement target material, kinetic change signals K(i) are measured for a large number of blood samples at the same time that true measured values T(i) of glucose concentration in the blood samples are obtained using equipment authorized as reference equipment (for example, YSI 2300). The correlation function denotes a function $f$ that minimizes the following equation for a total of n samples:

$$E_g = \sqrt{\frac{\sum_{i=1}^{n}(T(i) - f(K(i)))^2}{n}}$$

and this correlation function may be determined using a mathematical, logical or statistical method or an artificial intelligence method. Now, estimating and calculating glucose value for a new blood sample j using the determined optimal correlation function can be obtained as $M(j)=f\{K(j)\}$, which can be close to a value measured using the reference equipment.

Further, the present invention provides an apparatus for estimating feature values of a measurement target material using kinetic change information, comprising a kinetic information acquisition unit for acquiring kinetic change information; and a feature estimation unit for estimating the feature values of the measurement target material using both the kinetic change information and a previously determined correlation function.

Further, the present invention provides a computer-readable recording medium for storing a computer program for executing part or all of the methods.

In order to accomplish the above objects, the present invention provides an error correction method using kinetic change information for measuring the feature value of the first material, comprising acquiring kinetic change information appearing with passage of time during measurement; estimating feature values of a second material using both the kinetic change information and a previously determined first function; acquiring estimated errors of the feature values of the first material using both the feature values of the second material and a previously determined second function; and correcting the feature values of the first material measured without considering interference of the second material, by using the estimated errors of the first material.

The first function denotes a correlation between the feature values of the second material and the kinetic change information over time, and the second function denotes a correlation between the feature values of the second material and measurement errors of the first material.

In order to accomplish the above objects, the present invention provides an error correction apparatus, comprising a kinetic information acquisition unit for acquiring kinetic change information; a feature estimation unit for estimating feature values of a second material using both the kinetic change information and a previously determined first function; an estimated error acquisition unit for acquiring estimated errors of the feature values of the first material using both the feature values of the second material and a previously determined second function; and a feature correction unit for correcting the feature values of the first material measured without considering interference of the second material, by using the estimated errors of the first material.

The error correction apparatus includes a blood glucose meter as an embodiment, wherein the first material is glucose (blood sugar) in blood, the second material is a red blood cell in the blood, of which the feature value is the concentration which indicates hematocrit, and the kinetic change information is time-varying information of the chemical reaction during glucose concentration measurement.

That is, when the amount or concentration of blood sugar in blood is intended to be measured using an optical or electrochemical method, the measurement is interfered with by red blood cells in the blood. Even in blood actually having the same blood sugar, errors by which the measured blood sugar value appears differently due to hematocrit interference occur. Here, the present invention relates to an apparatus in which kinetic change information indicating the temporal change of measured blood sugar values is represented by a kinetic curve, hematocrit values are estimated based on the kinetic change information, errors are estimated using both the estimated hematocrit values and a separately obtained correlation function between the hematocrit values and measurement errors of the blood sugar, and then the errors are corrected by applying the estimated errors to the finally obtained blood sugar values.

Furthermore, in order to accomplish the above objects, the present invention provides a computer-readable recording medium for storing a computer program for executing part or all of the above methods.

Advantageous Effects

The present invention has the following excellent advantages.

First, the method and apparatus for estimating the feature values of a measurement target material using kinetic change information according to the present invention can acquire kinetic change information which is naturally obtained during the operating process of the apparatus, and can very simply and efficiently estimate and calculate the feature values of the measurement target material using a correlation function which has been previously obtained outside the apparatus and is included in the apparatus, without adding an additional chemical material using a separate manufacturing process, modifying the structure of a device and parts, or performing separate measurement for error elimination.

That is, the method and apparatus for estimating the feature values of a measurement target material using kinetic change information according to the present invention does not require a pre-process for eliminating an interfering substance, does not require chemical addition or the improvement or addition of a medium which was required in a measurement process to minimize interference, is capable of omitting hardware reinforcement for improving the accuracy of measurement results, and simply performs software-based processing, thus not only decreasing the costs of measuring devices and ensuring competitive power of products, but also enabling the present devised technology to be easily applied only by changing a software program without changing a chemical material, a medium or a device even in existing products.

Furthermore, the method and apparatus for estimating the feature values of a measurement target material using kinetic change information according to the present invention can estimate the feature values of the measurement target material close to true measured values using only the kinetic change of the measurement target material and a previously determined function, without performing a separate measurement or manufacturing process to eliminate the influence of a specific interfering substance for error correction.

Furthermore, the error correction method and apparatus using kinetic change information according to the present invention is advantageous in that it later corrects the influence of an interfering substance on the measurement of the feature values of a target material using a signal processing method based on a software program, without employing a scheme for reducing measurement errors via a method of previously eliminating an interfering substance based on a complicated process and device structure, thus efficiently eliminating errors from the measured values of the target material.

Furthermore, the error correction method and apparatus using kinetic change information according to the present invention is advantageous in that it can easily obtain kinetic change information during a process for measuring the feature values of a target material and can then very simply and efficiently eliminate errors from the measured values of the target material using previously determined functions, without adding a separate chemical material using a separate manufacturing process, modifying the structure of a device and parts, or performing a separate measurement for error elimination.

That is, the error correction method and apparatus according to the present invention does not require a pre-process for eliminating an interfering substance, does not require chemical addition or the improvement or addition of a medium which is required in a measurement process to minimize interference, is capable of omitting hardware reinforcement for improving the accuracy of measurement results, and performs software-based processing, thus not only decreasing the costs of measuring devices and ensuring competitive power of products, but also enabling the present devised technology to be easily applied only by changing a software program without changing a chemical material, a medium or a device even in existing products.

DESCRIPTION OF DRAWINGS

FIG. 4 is a table including true measured values (T) which are accurate feature values of blood sugar concentration, the estimated values (M) of blood sugar concentration estimated and calculated by the present invention, values (C) measured by a commercial blood glucose meter using the same glucose sensor, and the mean errors (E) among the values;

FIG. 10 is a table showing estimated hematocrit values, estimated blood sugar values and the errors thereof according to still another embodiment of the present invention;

BEST MODE

Figure 1:
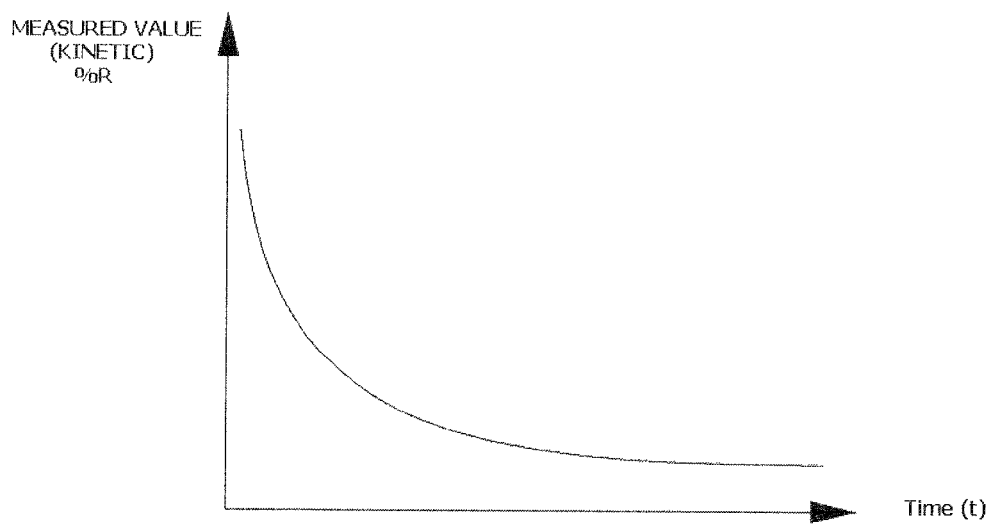
FIG. 1 is a graph showing temporal kinetic change along/over time resulting from a chemical reaction in the form of a curve (kinetic curve)

The terms used in the present invention have been selected as typical terms which are currently and widely used if possible, but, in a specific case, terms arbitrarily selected by the present applicant may be present. In this case, the meaning of the terms should be interpreted in consideration of the meaning thereof described or used in the detailed description of the present invention, rather than the simple names of the terms.

Hereinafter, the technical construction of the present invention will be described in detail with reference to the attached drawings and preferred embodiments.

However, the present invention is not limited to embodiments described here and may be embodied in other forms. The same reference numerals are used throughout the entire specification to designate the same components.

Terms used in the present specification are defined as follows.

The term "kinetic (change)" refers to a change in optical color or a change in electrochemical current or voltage, which appears with the passage of time in a method of measuring a specific chemical material contained in a sample using an optical or electrochemical method.

The term "feature value" refers to a numerical value which represents desired information about measurement target material or target material, and denotes, in the present invention, the concentration, amount, weight, amount ratio, etc. of a specific material.

The term "measurement target material or target material" refers to a material which should be finally measured from the sample of mixture such as blood, and which may include, for example, blood sugar (glucose), white blood cells or red blood cells in blood.

The term "interfering substance" refers to a substance which provides the cause of errors by interfering with the measurement of feature values of a measurement target material or a target material during a process for measuring the feature values, and may include, for example, red blood cells in blood, oxygen saturation, etc. which cause interference with the measurement of blood sugar.

FIG. 1 is a graph showing temporal kinetic change along/over time, appearing as a result of a chemical reaction, in the form of a curve according to an embodiment of the present invention.

When the concentration, amount or amount ratio (hereinafter referred to as a "feature value") of the measurement target material in a mixture of chemical materials is measured using an optical method, the results of a reaction with the measurement target material are measured using a change in the intensity of color. In this case, as the time passes, the intensity of color gradually changes. The feature values of the target material are calculated based on the intensity of color which is finally measured after a predetermined period of time has passed, or at the time point at which a specific condition is satisfied.

When the feature values of the measurement target material in the mixture of chemical materials are measured using an electrochemical method, the results of a reaction with the measurement target material are measured as the change in current or voltage which is an electrical signal. In the case of the change in the electrical signal, as the time passes, the signal gradually changes. The feature values of the measurement target material are calculated based on the value of the electrical signal that is finally measured after a predetermined period of time has elapsed or at the time point at which a specific condition is satisfied.

Optically or electrically measured values, which appear when two or more types of chemical materials react with one another, are called 'kinetic values.' A change in the measured values over time is called 'kinetic change'. Occasionally, the terms 'kinetic values' and 'kinetic change' may have the same meaning. Kinetic change can be represented by a kinetic curve, as shown in FIG. 1. In the case of an optical method, the term 'kinetic value' is also referred to as 'reflectance (% R)'.

The kinetic value according to the present invention is not limited to an optically or electrically measured value, and may include values measured by other methods satisfying the above definition.

A kinetic measurement curve may exhibit different curve slopes for respective samples. That is, the shapes of a curve are varying due to the differences between the features of the samples based on the composition of chemical mixtures in blood. That is, the kinetic change of the measurement target material may be influenced by the composition features of interfering substances contained in the mixtures. On the premise that such an influence causes the shapes of the curve to appear differently, research has been initiated and has then reached the present invention.

The present invention relates to a method of directly estimating and calculating the feature values of a measurement target material using kinetic change without estimating and calculating the feature values of a specific interfering substance as described above. That is, the present invention relates to a method of directly estimating and calculating the feature values of a measurement target material using kinetic change, which is expected to contain all information about both an interfering substance and the measurement target material, and a previously determined correlation function, without primarily estimating a specific interfering substance and secondarily correcting errors after estimating the feature values of the measurement target material.

Figure 2:
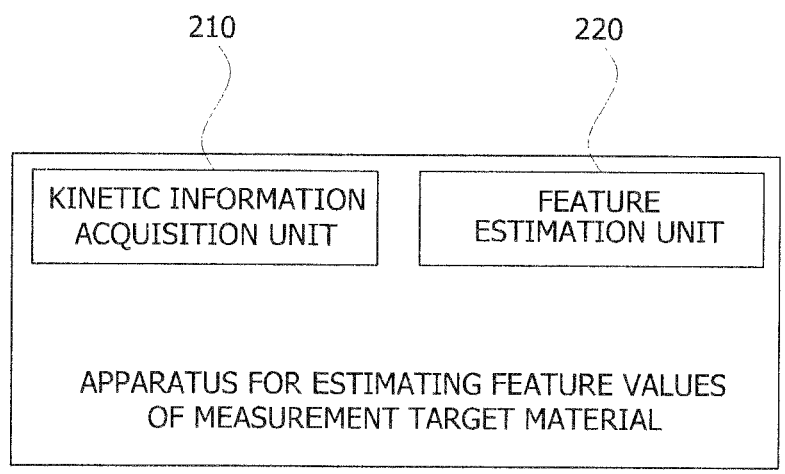
FIG. 2 is a block diagram showing an apparatus for estimating the feature values of a measurement target material using kinetic change information according to an embodiment of the present invention.

FIG. 2 is a block diagram showing an apparatus for estimating the feature values of a measurement target material using kinetic change information according to an embodiment of the present invention.

Referring to FIG. 2, the apparatus for estimating the feature values of a measurement target material includes a kinetic information acquisition unit 210 and a feature estimation unit 220.

The kinetic information acquisition unit 210 acquires information about the temporal change of results obtained from a procedure in which the measurement target material reacts with a reactant (hereinafter referred to as "kinetic change information").

The feature estimation unit 220 estimates and calculates the feature values of the measurement target material using the kinetic change information and a separately determined correlation function (a function represented by "$f$"). The correlation function $f$, which is determined using separate methods, is a function mathematically or logically indicating a correlation between the kinetic curves and true measured values, and is stored in the feature estimation unit 220.

The methods of obtaining such a correlation function $f$ used to estimate the feature values of the measurement target material according to the present invention may be implemented using very various ways, and embodiments thereof have been described above in the "Technical solution" section and will be described below.

Hereinafter, a method of estimating and calculating the feature values of the measurement target material according to the present invention, which is performed by the kinetic information acquisition unit 210 and the feature estimation unit 220 which are included in the apparatus for estimating the feature values of the measurement target material, will be described.

Figure 3:
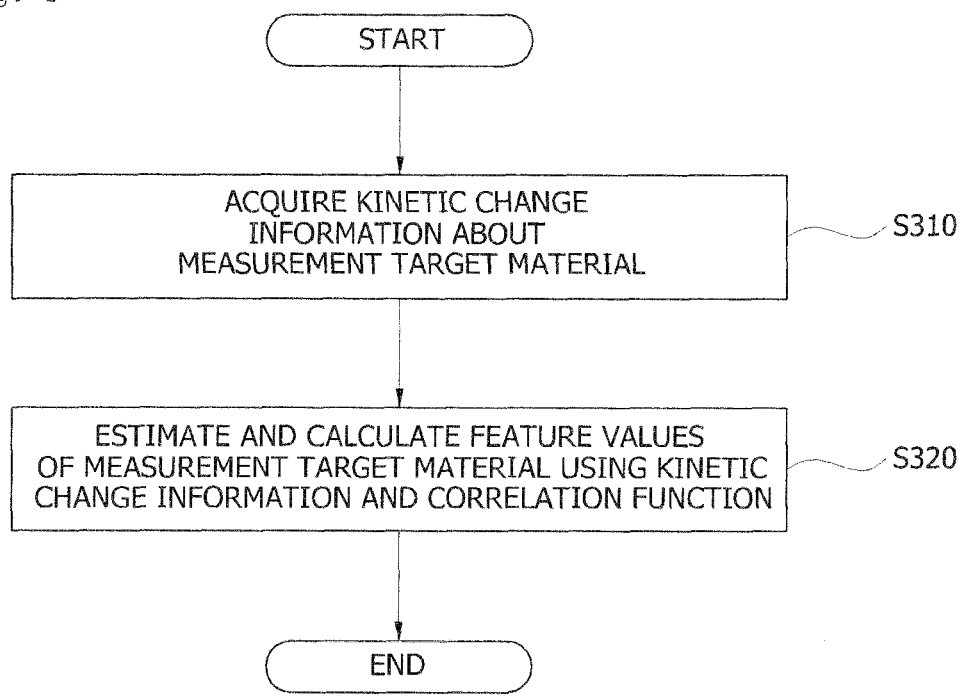
FIG. 3 is a flowchart showing a method of estimating the feature values of a measurement target material using kinetic change information according to an embodiment of the present invention.

FIG. 3 is a flowchart showing a method of estimating the feature values of the measurement target material using kinetic change information according to an embodiment of the resent invention.

As described above, kinetic change information can be acquired from a large number of samples sufficient enough thereof to be statistically accommodated, and the true measured values of the target material measured in an environment without interference by accurate reference equipment (i.e., YSI2300) can be obtained. When the optimal correlation between the kinetic change information and the true measured values of the measurement target material is known, the feature values of the measurement target material for new sample can be estimated and calculated using the kinetic change information obtained from the new sample and the function.

For the purpose of providing a clearer description, the method of estimating the feature values of the measurement target material according to the present invention will be described below together with numerical expressions. Here, the symbol "□" is a symbol indicating that values in the left and right terms are similar to each other, and functions and values to be used are defined as follows.

First, when a kinetic curve (or kinetic change information) acquired from a large number (n) of samples sufficient enough to be statistically accommodated via a separate procedure is denoted by K(i), and each accurately measured value obtained in an environment without interference by a reference equipment is denoted by T(i), an optimal correlation function $f$ between kinetic changes and accurately measured values for all of the samples denotes a function minimizing the following RMS error:

$$E_g = \sqrt{\frac{\sum_{i=1}^{n}(T(i) - f(K(i)))^2}{n}}$$

and this function can be determined by a mathematical, logical or statistical method or an artificial intelligence method.

Using the optimal correlation function determined by the above method, the feature value of glucose which is estimated and calculated for a newly supplied blood sample j can be obtained as $M(j) = f\{K(j)\}$ and this value is expected to close to the value measured using reference equipment. That is, when the optimal correlation function $f$ between the true measured values of the measurement target material and the kinetic curve is known in advance using a method based on a mathematical or logical rule, the feature value M close to the true measured value T can be obtained for the measurement target material contained in the newly supplied sample.

Hereinafter, the method of estimating and calculating the feature values of the measurement target material when a new sample is supplied will be described with reference to the apparatus for estimating the feature values of the measurement target material according to the present invention, as depicted in FIG. 1, and the flowchart of the method of estimating the feature values of the measurement target material, as depicted in FIG. 3.

First, the kinetic information acquisition unit 210 acquires the kinetic change information about a measurement target material which is desired to be measured at step S310. The kinetic change information is information in which the feature values of the measurement target material vary over time and which is represented in the form of a kinetic curve.

The feature estimation unit 220 estimates the feature values M of the measurement target material using both the kinetic change information acquired from the measurement of the measurement target material and the previously determined function $f$, as described at step S320.

Methods of obtaining the correlation function $f$ may be implemented in various ways, and any functions can be possible as long as they can individually minimize errors $E_g$ defined in the following Equation 1, $$E_g = \sqrt{\frac{\sum_{i=1}^{n}(T(i) - M(i))^2}{n}} \quad <\text{Equation 1}>$$

where i is an index indicating each sample, T(i) is a true measured value which is an accurate feature value of the measurement target material, and M(i) is a feature value estimated and calculated for the measurement target material by using $f$ on the basis of kinetic change. That is, $E_g$ denotes an average error which is computed from the accumulation of measurement errors for a total of n samples.

Further, in methods of obtaining the correlation function $f$, any functions can be possible as long as they can individually minimize the error $E_g$ defined in the following Equation 2.

$$E_g = \frac{1}{n}\sqrt{\sum_{i=1}^{n}(T(i) - f(K(i)))^2} \quad <\text{Equation 2}>$$

The RMS error $E_g$ denotes a value obtained by accumulating the differences between the true measured values T(i) obtained by the reference equipment and the measured values $M(i) = f\{K(i)\}$ estimated and calculated using the function $f$ on the basis of the kinetic change for a large number of samples. The function $f$ is a function that minimizes the RMS error and can be obtained by various mathematical or logical methods, and thus there may occur a difference in the absolute minimum value of $E_g$ depending on the methods to find the function f. That is, a difference in the accuracy of estimated values may occur depending on which method has been used to obtain the function. The present invention includes all methods of estimating and calculating the feature values of the measurement target material by applying such a function to the kinetic change information, regardless of which method has been used to obtain such a function. In other words, the present invention claims the method of estimating and calculating method using the kinetic change information as the input to the correlation function f.

As described above, the method of estimating the feature values of the measurement target material according to the present invention is characterized in that it includes a series of procedures of (1) obtaining the function $f$, which indicates a correlation between kinetic change K and true measured values T that are accurate feature values of the measurement target material, from a large amount of data previously measured, and of (2) when a request for the measurement of the feature values of the measurement target material occurs for a new mixture sample, K is first acquired during the measurement, and then the function f is applied to K on order to estimate and calculate the feature value M of the measurement target material, and thus the kinetic change information and the correlation function $f$ are used in these procedures. Hereinafter, an embodiment in which the method and apparatus for estimating the feature values of the measurement target material according to the present invention is used in blood glucose measurement will be described.

Next, in order to prove the effects of the estimation of feature values for blood glucose measurement by applying the technology of the present invention, the results of comparative experiments with commercial products using the same glucose sensor will be described below.

FIG. 4 is a table including true measured values T which are accurate feature values of blood sugar concentration measured by YSI 2300, the feature values M of blood sugar estimated and calculated by the present invention, values C measured by a commercial blood glucose meter that uses the same glucose sensor, and the average errors E among those values. Here, ME denotes the square (error) of the differences between the feature values M of the measurement target material estimated according to the present invention and the true measured values T, and CE denotes the square (error) of the differences between the values C measured by the commercial blood glucose meter and the true measured values T.

As shown in FIG. 4, it can be seen that most of feature values M estimated by the present invention have values closer to the true value T than the value C measured by the commercial blood glucose meter, and in terms of average errors presented in the most bottom of the table, the average error of the feature values M estimated according to the present invention are smaller than that of the values C measured by the commercial blood glucose meter.

Figure 5:
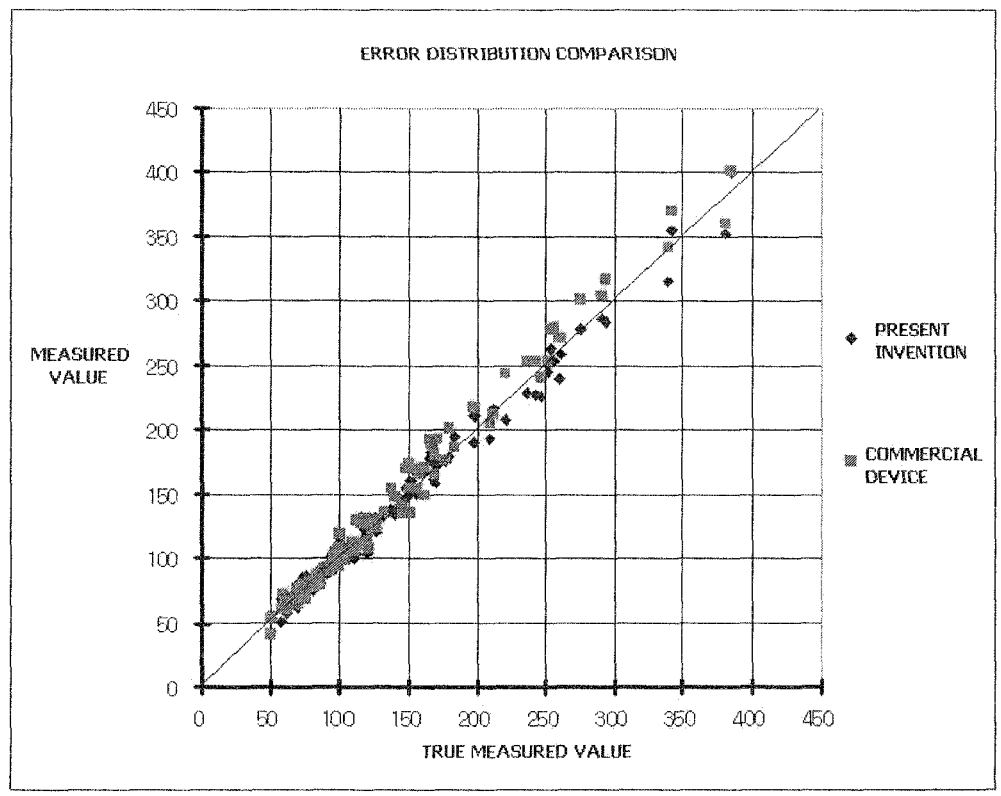
FIG. 5 is a graph showing error distributions with the plot of paired value of accurate blood sugar values ('true measured values' on the X axis) measured by reference equipment YSI 2300, and blood sugar values ('measured values' on the Y axis) measured by either the method of the present invention or conventional method.

FIG. 5 illustrates another expression of the data shown in the table of FIG. 4, and is a graph showing the accurate blood sugar values measured by reference equipment YSI 2300 ('true measured values' on the X axis), and the blood glucose values measured by the portable commercial device and estimated by the method of the present invention ('measured values' on the Y axis), in which each point presents an individual blood sample. In this graph, any point on the line of upper-right diagonal indicates no measurement error for the corresponding blood sample.

That is, as the individual measured values are located closer to the line of upper-right diagonal, the measurement result is better.

As shown in FIG. 5, it can be seen that blood sugar values calculated by the method of the present invention make the point closer to the line of upper-right diagonal than those measured by the commercial portable measuring device, thus showing that the measurement errors of the blood sugar values calculated by the method of the present invention are smaller than those made by using the commercial portable measuring device.

MODE FOR INVENTION

Another embodiment of the present invention relates to a method of estimating the feature values of an interfering substance using kinetic changes having different forms depending on the feature values of interfering substances and correcting the measurement errors in the feature values of a target material using a correlation between the feature values of the interfering substance and the errors of the target material.

Figure 6:
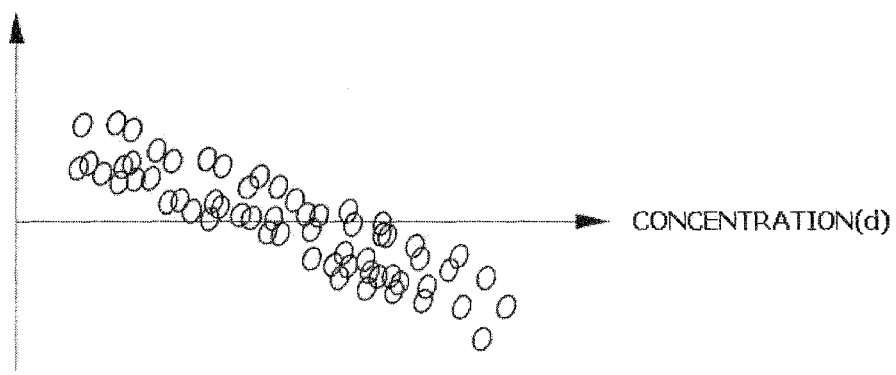
FIG. 6 is a graph showing a correlation between the concentration of an interfering substance (X-axis) and the measurement errors of the feature values of a target material (Y-axis) according to another embodiment of the present invention.

FIG. 6 is a graph showing a correlation example between the concentration of an interfering substance and measurement errors in the feature values of a target material according to another embodiment of the present invention.

The magnitude of measurement errors caused by the interference of the interfering substance varies depending on the feature values of the interfering substance, and appears to increment or decrement from the accurately measured values of the target material under the condition that the influence of the interfering substance is eliminated. That is, there is a correlation between the feature values of the interfering substance and the magnitude of measurement errors. FIG. 6 illustrates one example indicating such a correlation.

Referring to FIG. 6, when the feature value of the interfering substance (represented by "concentration (d)" in FIG. 6) is small, a measurement error in the feature value of a target material has a positive value (an incremental error), whereas when the feature value of the interfering substance is large, a measurement error has a negative value (a decremental error). Here, the measurement error denotes the difference between the feature value of the target material measured using a mixture containing an interfering substance and the feature value of the target material measured without the interfering substance by reference equipment. An error distribution depending on the concentration of the interfering substance of FIG. 6 is only exemplary, and the present invention includes the tendencies of error distribution different from that of FIG. 6.

Therefore, the correlation between the feature values of the interfering substance and the measurement errors of the target material can be represented by mathematical, logical rules, etc. In addition, when the feature values of the interfering substance can be known, the measurement errors of the target material can be obtained using the correlation, and the feature values of the target material containing errors due to the interfering substance can be corrected using the measurement errors.

Figure 7:
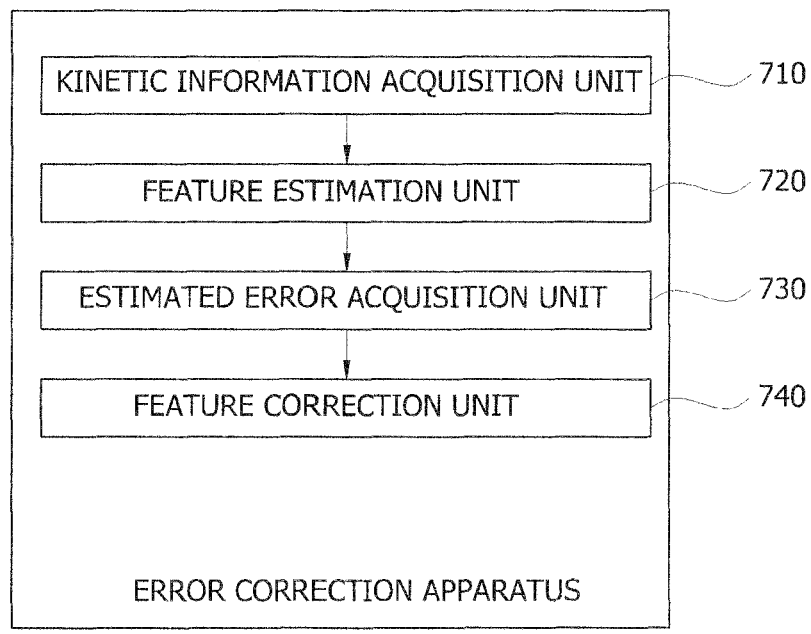
FIG. 7 is a functional block diagram showing an error correction apparatus using kinetic change information according to a further embodiment of the present invention.

FIG. 7 is a block diagram showing an error elimination apparatus using kinetic change information according to a further embodiment of the present invention.

Referring to FIG. 7, the error elimination apparatus includes a kinetic information acquisition unit 710, a feature estimation unit 720, an estimated error acquisition unit 730 and a feature correction unit 740.

The kinetic information acquisition unit 710 acquires kinetic information during a procedure for measuring a target material, and also obtains time-varying information of the kinetic (hereinafter referred to as "kinetic change information").

The feature estimation unit 720 estimates the feature values of the interfering substance using both the kinetic change information and a previously determined first function (a function represented by "g"). The first function g determined using a separate method is a function for mathematically or logically indicating the correlation between a kinetic curve and the feature values of the interfering substance, and can be implemented in the error correction apparatus.

The estimated error acquisition unit 730 acquires the estimated errors of the target material using both the estimated feature values of the interfering substance and a previously determined second function (a function represented by "$f$"). The second function $f$ indicates the correlation between the feature values of the interfering substance and the estimated errors of the target material, and may be previously determined using a mathematical or logical method and may be also implemented in the error correction apparatus.

Methods of obtaining the correlation functions $f$ and g used to correct the measurement errors of the target material caused by the interference of an interfering substance may be implemented using a variety of methods. Embodiments of the methods of obtaining the functions $f$ and g will be described later.

The feature correction unit 740 corrects the feature values of the target material, which have been acquired without considering the influence of the interference of the interfering substance, by utilizing the estimated errors of the target material acquired by the estimated error acquisition unit 730.

Next, the error correction method of the present invention which is performed by the kinetic information acquisition unit 710, the feature estimation unit 720, the estimated error acquisition unit 730 and the feature correction unit 740 which are included in the error correction apparatus will be described below.

Figure 8:
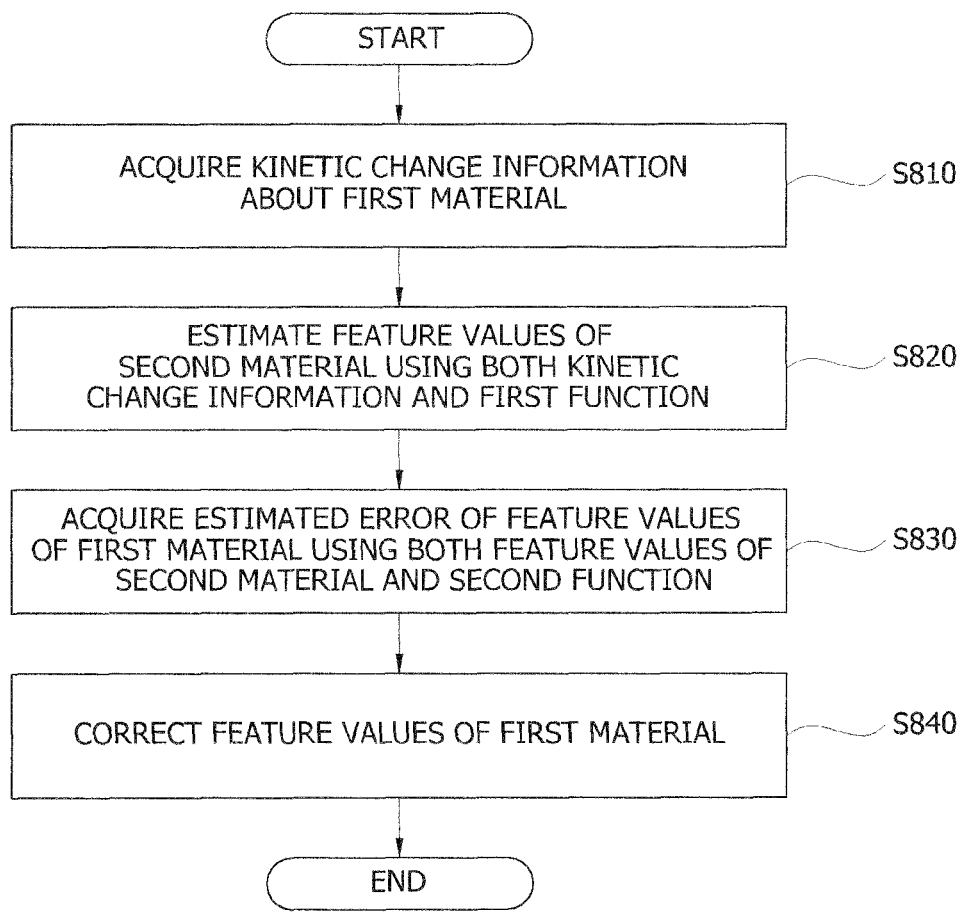
FIG. 8 is a flowchart showing an error correction method using kinetic change information according to yet another embodiment of the present invention.

FIG. 8 is a flowchart showing an error elimination method using kinetic change information according to yet another embodiment of the present invention.

As described above, if the feature values of an interfering substance can be estimated using kinetic change information, and also if a correlation between the feature values of the interfering substance and error which is the difference between the accurate feature values of a target material measured in an environment in which interference is eliminated and the feature values of the target material measured in an environment in which interference is included, is known, then the measurement errors of the target material can be estimated using the correlation. By applying the estimated error to the feature values of the target material measured in the environment with the interference, the interference-eliminated feature values can be obtained.

For the purpose of providing a clearer description, the error correction method according to the present invention is described using numerical expressions as follows. Here, the symbol "□," is indicating that values in the left and right terms are similar to each other, and functions and values to be used are defined as follows.

Let T be the accurately measured feature value of a target material without an error, and M be the measured feature value of the target material with an error, then the error D is defined as D=M−T. Let K be a kinetic curve (or kinetic change information), and d be the feature value of an interfering substance, then a first function g indicating a correlation between the feature value of the interfering substance and the kinetic curve is represented by d=g(K). And, a second function $f$ indicating a correlation between the feature value of the interfering substance and the measurement error of the target material is represented by D=f(d).

Therefore, the feature value of the interfering substance estimated from kinetic change information acquired from a newly supplied sample is defined by d'=g(K), the estimated error of the target material is defined by D'=$f$(d')=$f${g(K)} □D, and the corrected feature value of the target material can be obtained by (C=M−D')□(M−D=T).

That is, if both the correlation function g(K) between the feature value of the interfering substance and the kinetic curve, and the correlation function f(d) between the feature value of the interfering substance and the measurement error of the target material are known in advance using a method based on a mathematical or logical rule, then the estimated value d' of the feature value of the interfering substance in the newly supplied sample can be calculated, the estimated error D' can be obtained based on the estimated value d', and a value close to the accurate feature value T can be obtained by subtracting the estimated error D' from the measured value M including the error due to the interference.

Hereinafter, the error elimination method will be described with reference to the error correction apparatus of FIG. 7 and the flowchart of the error elimination method of FIG. 8 according to the present invention. First, the kinetic information acquisition unit 710 acquires the kinetic change information about a target material desired to be measured (hereinafter referred to as a "first material") at step S810. The kinetic change information is the time-varying feature values of the measurement target material and is represented by a kinetic curve.

The feature estimation unit 720 estimates the feature values d' of the interfering substance (hereinafter referred to as a "second material") using both the kinetic change information acquired during the measurement of the first material and a previously determined first function g at step S820.

Then, the estimated error acquisition unit 730 acquires estimated errors corresponding to the feature values of the first material using both the feature values of the second material and a previously determined second function f at step S830. The feature correction unit 740 corrects the feature values measured on the first material using the estimated errors at step S840.

The methods of obtaining the two correlation functions, that is, the first function g and the second function f, are variously implemented, and any functions can be used as long as they can minimize the functions $E_g$ and $E_f$ defined in the following Equations 3 and 4, $$E_g = \sum_i [d(i) - g\{K(i)\}]^2 = \sum_i [d(i) - d'(i)]^2 \qquad < \text{Equation 3} >$$

where i is an index indicating each mixture sample, d(i) is the accurately measured feature value of the second material, and d'(i)=g{K(i)} is the feature value of the second material estimated by the first function g using the kinetic change information. That is, $E_g$ denotes the accumulation of errors of the second material.

$$E_f = \sum_i [D(i) - D'(i)]^2 \qquad < \text{Equation 4} >$$
$$= \sum_i [D(i) - f\{d'(i)\}]^2$$
$$= \sum_i [D(i) - f\{g[K(i)]\}]^2$$

where i is an index indicating each mixture sample, D(i) is the accurate measurement error of the first material obtained by using a reference measuring device, and f{d'(i)} is the estimated error of the first material obtained using both the estimated value d' of the second material, which is estimated using the first function g based on the kinetic change information, and the second function f. That is, $E_f$ denotes the accumulation of errors of the first material, defined as the difference between the accurate value and the estimated value.

Each of the two error Equations is represented by the accumulated value of the differences between accurate values and estimated values for a large number of samples (hereinafter referred to as "total error"). The first and second functions are the functions satisfying the minimization of total error for all samples. The functions for minimizing such a total error may be obtained by various the mathematical or logical methods, and thus the difference between the absolute minimum values of $E_g$ and $E_f$ may occur. That is, depending on which method has been used to obtain the two functions, the accuracy of error correction may be different. The present invention includes any methods of correcting errors using the two functions regardless of which method has been used to obtain them and kinetic change information as the input to the first function.

As described above, the error correction method according to the present invention is characterized in that it includes a series of procedures of (1) obtaining a first function g(K), which indicates a correlation between kinetic change and the feature values of the second material, from a large amount of measured data that has been previously acquired, (2) also obtaining a function f(d), which indicates a correlation between the accurate feature values of the second material and the accurate measured errors of the first material, from a large amount of data previously measured, (3) when a request for the measurement of the feature values of the first material occurs for a new mixture sample, acquiring K during the measurement of the feature values and estimating the feature values d' of the second material using the function g(K), (4) obtaining the estimated errors D'=f(d') of the first material using both the estimated feature values d' of the second material and the second function f, and (5) obtaining the feature values C of the first material in which errors caused by interference are corrected by subtracting the estimated errors f(d') from the feature values M of the first material measured without considering the interference, and in that during these procedures, two correlation functions g(K) and $f(x)$ are used. Hereinafter, an embodiment in which the error correction method and apparatus according to the present invention is used for blood glucose measurement will be described.

In order to more apparently describe the above explanation, those procedures are represented by numerical expressions as follows. Here, the symbol "☐" is indicating that values in the left and right terms are similar to each other.

accurate value T, error-containing measured value M of target material (first material), and interference error D: M=T+D or T=M−D kinetic curve: K feature value of interfering substance (second material): d correction function between the feature of the interfering substance (second material) and kinetic curve g: d=g(K)

correlation function between the feature of the interfering substance (second material) and the interference value (error) $f$: D=$f$(d)

estimated feature value of a interfering substance (second material) for a new sample d': d'=g(K)

estimated error for the target material (first material) D': D'=$f$(d")=$f${g(K)}☐D corrected value for the target material (first material) C: C=M−D'☐M−D=T That is, if the correlation function g(K) between the feature value of the interfering substance and the kinetic curve and the correlation function $f$(d) between the feature value of the interfering substance and the error value for the first material are known in advance using a method based on a mathematical or logical rule, then the estimated feature value d' of the interfering substance for a new measured sample can be calculated, so that the estimated error D' can be obtained based on the estimated feature value and a value close to the true value T can be obtained by subtracting the estimated error D' from the measured value M containing the error caused by interference.

Figure 9:
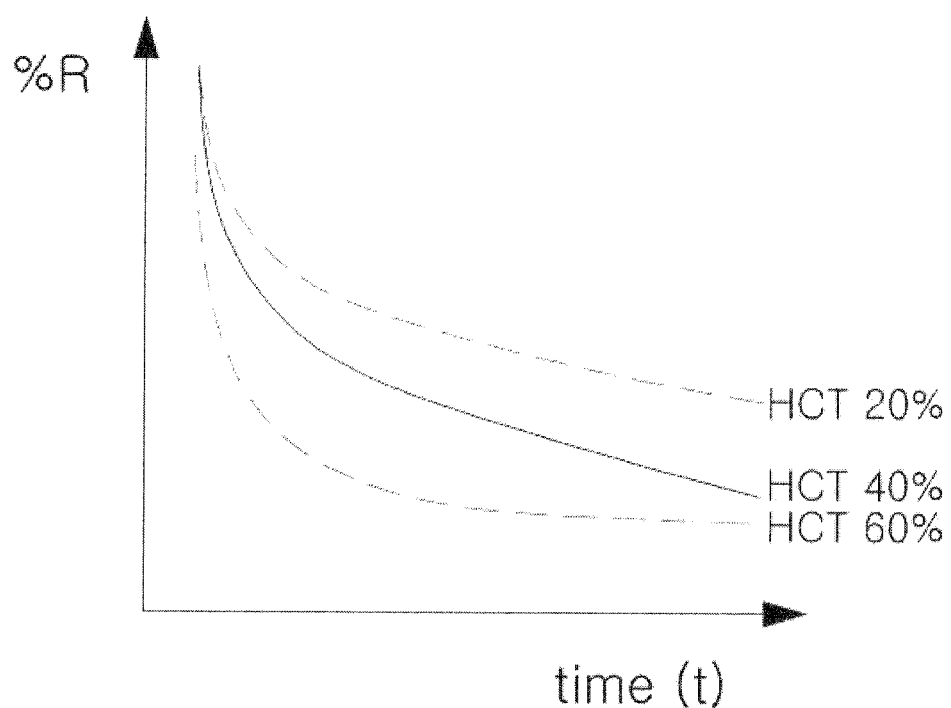
FIG. 9 is a graph showing a relationship between kinetic change information and the hematocrit concentration of blood according to still another embodiment of the present invention.

FIG. 9 is a graph showing a relationship between kinetic change information and the hematocrit concentration of blood according to still another embodiment of the present invention.

When blood sugar (or glucose) concentration of blood is intended to be measured using a glucose sensor and a portable blood glucose meter, red blood cells act as an interfering substance, so that errors in measured blood sugar values appear differently due to the hematocrit interference. However, with the different the concentration of red blood cells contained in blood, kinetic change information for blood sugar measurement appears differently. Referring to FIG. 9, when the hematocrit concentration is 20%, the concentration of blood sugar slowly decreases over time, whereas when the hematocrit concentration is 60%, the concentration of blood sugar rapidly decreases over time. Therefore, even in the case of two blood samples having the same blood sugar value, blood sugar values measured at a predetermined time point may differ. On the contrary, two blood samples having different blood sugar values may be measured to have the same blood sugar value.

If the correlation between the hematocrit concentration and the kinetic change information in measurement of blood sugar is used, the hematocrit concentration indicating the ratio of the volume of red blood cells to the volume of the blood can be estimated from the kinetic change information. Further, if a relationship between the estimated hematocrit concentration and the error of the measured blood sugar values is used, the error contained in the measured blood sugar values can be eliminated.

That is, when the blood sugar concentration of whole blood is measured using a glucose sensor and a portable self-blood glucose meter which cannot perfectly eliminate the influence of hematocrit, error values caused by the influence of hematocrit are added to the accurate true values which can be measured by an expensive accurate chemical analyzer capable of eliminating the influence of hematocrit (for example YSI2300), and then blood sugar concentration is finally determined with the meter.

In this case, the conventional technology has focused its effort on the improvement of quality and performance of a glucose sensor used as a medium of measurement so as to minimize the influence of hematocrit. However, when the present invention is used, it is implemented as a new blood glucose meter which corrects blood glucose measurement errors using a simple numerical analysis method or, alternatively, it is simply implemented on the existing portable devices by adding the error correction method of reducing the hematocrit interference.

Hereinafter, in order to prove the effects of error correction related to blood sugar measurement using the technology of the present invention, the results of comparative experiments with a commercial product that uses the same glucose sensor as the present invention will be described.

Figure 11:
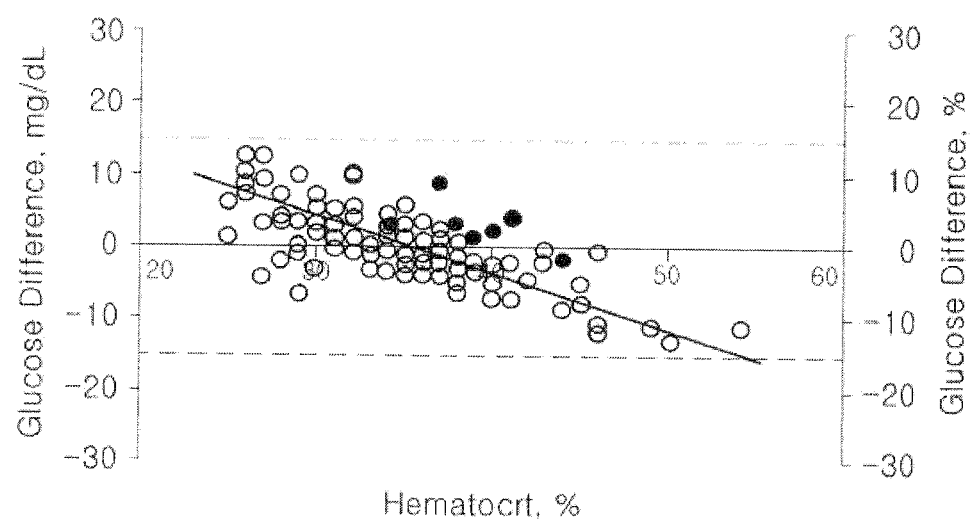
FIG. 11 is a graph showing a positive or negative error distribution tendency depending on hematocrit concentration (same as FIG. 6) according to still another embodiment of the present invention.

First, drawings presenting the results of the experiments are described. FIG. 10 is a table showing accurate hematocrit values d, accurate blood sugar values T measured by YSI2300, both hematocrit values d' and error-corrected values of blood sugar C estimated by the present invention, the errors of those two estimated values, glucose values measured by a commercial blood glucose meter that uses the same glucose sensor, and the errors of commercial blood glucose meter, those values being obtained from whole blood samples. FIG. 11 is a graph showing the interference of hematocrit concentration with the measurement of blood sugar, which shows that when the hematocrit concentration is low, a positive error is caused, whereas when the hematocrit concentration is high, a negative error is caused (reference: Richard F. Louie et al, "point-of-Care Glucose Testing: Effects of Critical Care Variables, Influence of Reference Instruments, and a Modular Glucose Meter Design", Arch. Pathol. Lab. Med, Vol. 124, February 2000).

Figure 12:
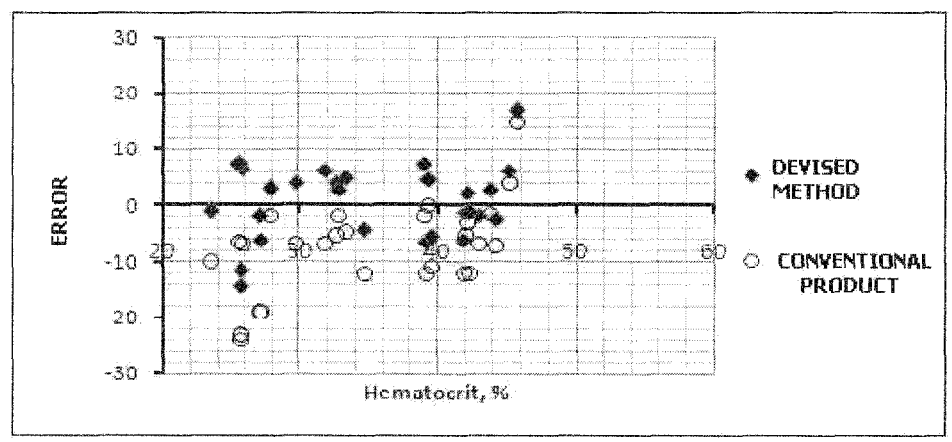
FIG. 12 is a graph showing (a) error distributions and (b) normalized error distributions depending on hematocrit concentration according to still another embodiment of the present invention.
Figure 12:
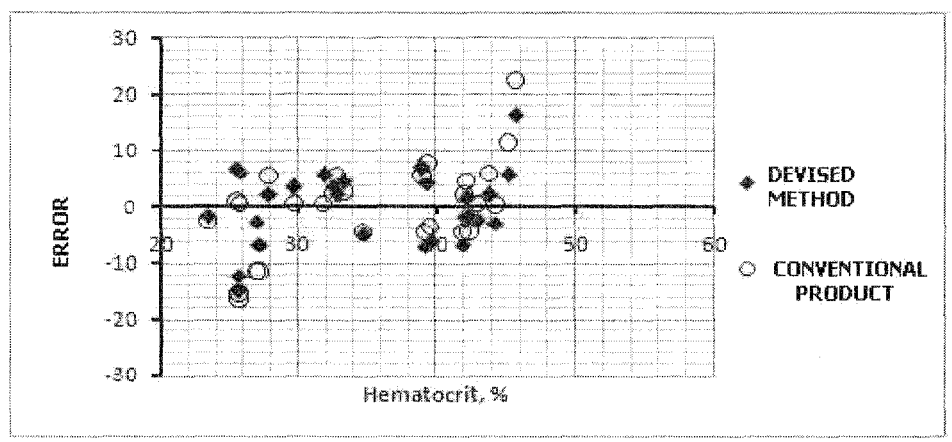
Figure 13:
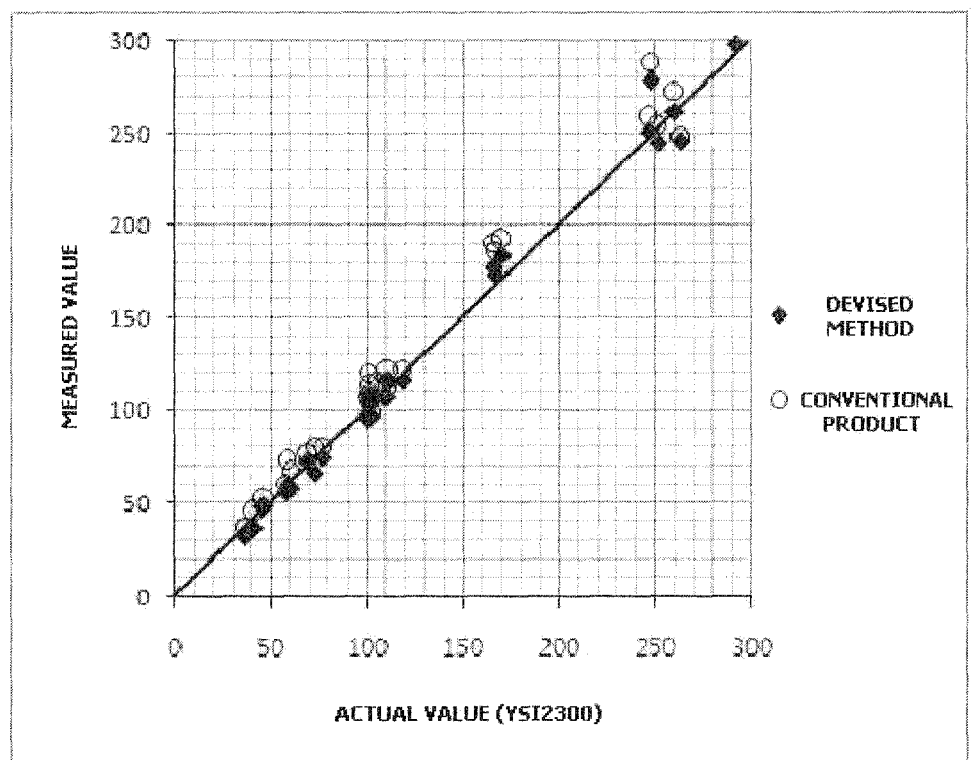
FIG. 13 is a graph showing the comparison of error distributions according to still another embodiment of the present invention with error distributions of a conventional method.

FIG. 12 is a graph showing (a) error distributions and (b) normalized error distributions with respect to hematocrit concentration resulted from another embodiment of the present invention and the conventional commercial product, and FIG. 13 is a graph showing the accurate blood sugar values ('actual values' on the X axis) measured by reference equipment YSI2300, and the blood glucose values measured by the portable commercial device and estimated by the method of the present invention ('measured values' on the Y axis), in which each point presents an individual blood sample. Drawings show that any point on the line of upper-right diagonal indicates no measurement error for the corresponding blood sample. That is, as measured values are placed closer to the upper line of upper-right diagonal, the measurement result is better.

Comparative experiments are conducted as follow. First, 27 samples, which provide the combinations of low, medium, and high values for both hematocrit and glucose concentrations, were arbitrarily selected from a large number of samples, and the following four types of values were measured from each sample in the group of 27.

A first value is the accurate hematocrit concentration of blood, which is measured by accurate hematocrit measuring equipment used in the clinical pathology room of a hospital.

A second value is the blood sugar measured by accurate measuring equipment (YSI2300) used as reference equipment for blood sugar measurement.

A third value is the blood sugar measured by a commercial product which is commercially sold (that is, a glucose sensor and a measuring device matching therewith). In order to eliminate the problem of reproducibility occurring due to the defects of a glucose sensor itself, the medium value from three repetitive measurements. In the present comparative experiments, measurements were conducted using three sensors to minimize the problem of the reproducibility of the glucose sensor itself. Only the cases in which the three measurement results are similar to each other within a predetermined range were considered, and among them, the cases in which the value measured by the commercial product was the medium among those three were chosen.

A fourth value is the kinetic change information collected from a conventional measuring device while the third value is measured using. Kinetic information was measured every 0.5 seconds and was measured for a total of 13 seconds.

The three measured values (values from YSI2300, hematocrit concentration, and values measured by the commercial product), and the estimated hematocrit concentration, estimated blood sugar values and the errors thereof which are obtained by the method of the present invention are shown in the table of FIG. 10. FIG. 10 shows that Root-Mean-Squared-Error (RMSE) values of the blood sugar values estimated by the present invention and the values measured by the conventional commercial product are 5.32476 and 8.9148, respectively, thus indicating that the blood sugar errors caused by the method of the present invention are entirely lower than those of the conventional commercial product.

FIG. 12(a) illustrates errors in blood sugar measurement by the method of the present invention and the conventional product with respect to hematocrit concentration, which is another presentation of the table of FIG. 10, wherein the method of the present invention generally has an error distribution which does not lean toward a negative (−) or a positive (+) value, but the conventional product has a tendency of leaning toward a negative (−) value. FIG. 12(b) illustrates a normalized error distribution so that error values are displayed on the basis of the mean value of the errors to be zero so as to eliminate a negative or positive tendency from the results of FIG. 12(a). As shown in FIGS. 12(a) and (b), it can be seen that the occurrence of negative or positive errors shown in FIGS. 6 and 11 has been eliminated for both cases of present invention and existing conventional product, and that the errors from the present invention are smaller than those from the conventional product, thus proving the effects of the method devised by the present invention.

FIG. 13 is a diagram showing the table of FIG. 10 and the error distribution of FIG. 12 in another form. In this drawing, an upper right portion of a diagonal shows that the measured values (on the Y axis) are identical to accurately measured values (on the X axis), and that when the points are located on line of the upper-right diagonal, there is no error in corresponding blood samples. That is, as measured values are located closer to the upper-right diagonal line, the measurement result is better. The drawing shows that the blood sugar values estimated by the method devised in the present invention are closer to the upper-right diagonal line than the conventional commercial product, and this is one experimental result which proves the effects of the method devised by the present invention.

As shown in the results of the above comparative experiments, the method of the present invention which estimates hematocrit from kinetic change information and corrects the errors of the measuring device based on this estimated hematocrit can reduce the measurement errors of the conventional commercial product, thus improving the performance.

Although the preferred embodiments of the present invention have been explained and illustrated, the present invention is not limited to the above embodiments and various modifications and changes are possible by those skilled in the art based on the spirit of the invention.

The invention claimed is:

1. A non-transitory computer-readable recording medium storing a computer program for executing a method of estimating feature values of a measurement target material used in an apparatus for estimating feature values of a measurement target material using kinetic change information in a chemical reaction, the method comprising:
   acquiring kinetic change information related to feature values of a measurement target material; and
   estimating the feature values of the measurement target material using both the kinetic change information and a previously determined correlation function,
   wherein the kinetic change information denotes a change in electrochemical current or voltage of the measurement target material with the passage of time,
   wherein the feature values denotes a numerical value which represents at least one of the group consisting of a concentration, an amount, a weight, and an amount ratio of the measurement target material, and
   wherein the previously determined correlation function denotes a function which indicates a correlation between the kinetic change information and true measured values that are feature values of the measurement target material from a large amount of data previously measured.

2. The method according to claim 1, wherein the correlation function denotes a correlation between true measured values of the measurement target material and the kinetic change information, the true measured values of the measurement target material being obtained from a plurality of samples in an environment in which interference is eliminated.

3. The method according to claim 2, wherein the correlation function minimizes an average error ($E_g$) defined in the following Equation 1:

$$E_g \sqrt{\frac{\sum_{i=1}^{n}(T(i)-M(i))^2}{n}} \qquad < \text{Equation 1} >$$

where n is a total number of samples, i is an index indicating each sample, T(i) is a true measured value of the measurement target material, and M(i) is a feature value of the measurement target material estimated by the correlation function and the kinetic change, wherein $E_g$ denotes an average error over the total of n samples.

4. The method according to claim 1, wherein the measurement target material is glucose in blood.

5. The method according to claim 4, wherein each of the feature values is concentration and the kinetic change information is information in which a measured value of the glucose concentration changes with the passage of time.

6. An apparatus for estimating feature values of a measurement target material using kinetic change information, comprising:
a kinetic information acquisition unit for acquiring kinetic change information related to feature values of a measurement target material; and
a feature estimation unit for estimating the feature values of the measurement target material using both the kinetic change information and a previously determined correlation function.

7. The apparatus according to claim 6, wherein the correlation function denotes a correlation between true measured values of the measurement target material and the kinetic change information.

8. The apparatus according to claim 6, wherein the measurement target material is glucose in blood.

9. The apparatus according to claim 8, wherein each of the feature values is concentration and the kinetic change information is information in which a measured value of the glucose concentration changes with the passage of time.

10. A non-transitory computer-readable recording medium storing a computer program for executing an error correction method used in an error correction apparatus using kinetic change information, comprising:
acquiring kinetic change information related to feature values of a first material;
estimating feature values of a second material using both the kinetic change information and a previously determined first function;
acquiring estimated errors of the feature values of the first material using both the feature values of the second material and a previously determined second function; and
correcting the feature values of the first material measured without considering interference of the second material, by using the estimated errors of the first material,
wherein the kinetic change information denotes a change in electrochemical current or voltage of a measurement target material with the passage of time,
wherein the feature values denotes a numerical value which represents at least one of the group consisting of a concentration, an amount, a weight, and an amount ratio of the measurement target material, and
wherein the previously determined correlation function denotes a function which indicates a correlation between the kinetic change information and true measured values that are feature values of the measurement target material from a large amount of data previously measured.

11. The error correlation method according to claim 10, wherein the first function denotes a correlation between the feature values of the second material and the kinetic change information.

12. The error correlation method according to claim 11, wherein the first function minimizes a value ($E_g$) defined in the following Equation 3:

$$E_g = \sum_i [d(i) - g\{K(i)\}]^2 = \sum_i [d(i) - d'(i)]^2 \quad <\text{Equation 3}>$$

where i is an index indicating each mixture sample, d(i) is an accurately measured feature value of the second material, and d'(i)=g{K(i)} is a feature value of the second material estimated by the first function g using the kinetic change information, wherein $E_g$ denotes accumulation of errors of the second material for all samples.

13. The error correction method according to claim 10, wherein the second function denotes a correlation between the feature values of the second material and measurement errors of the first material.

14. The error correction method according to claim 13, wherein the second function minimizes a value ($E_f$) defined in the following Equation 4, $$E_f = \sum_i [D(i) - D'(i)]^2 \quad <\text{Equation 4}>$$
$$= \sum_i [D(i) - f\{d'(i)\}]^2$$
$$= \sum_i [D(i) - f\{g[K(i)]\}]^2$$

where i is an index indicating each mixture sample, D(i) is an accurately measured error of the first material which can be calculated using both the value obtained by a accurate reference measuring device and value obtained by the devised device, and f{d'(i)} is an estimated error of the first material obtained using both an estimated value d' of the second material, which is estimated using both the first function g and the kinetic change information, and the second function f, wherein $E_f$ denotes accumulation of errors of the first material over all samples, defined as a difference between an accurate value and an estimated value.

15. The error correction method according to claim 10, wherein the first material is glucose in blood, and the second material is a red blood cell in blood.

16. The error correction method according to claim 15, wherein each of the feature values is concentration and the kinetic change information is information in which a measured value of the glucose concentration changes with the passage of time.

17. An error correction apparatus, comprising: a kinetic information acquisition unit for acquiring kinetic change information related to feature values of a first material; a feature estimation unit for estimating feature values of a second material using both the kinetic change information and a previously determined first function; an estimated error acquisition unit for acquiring estimated errors of the feature values of the first material using both the feature values of the second material and a previously determined second function; and a feature correction unit for correcting the feature values of the first material measured without considering interference of the second material, by using the estimated errors of the first material.

18. The error correction apparatus according to claim 17, wherein the first function denotes a correlation between the feature values of the second material and the kinetic change information.

19. The error correction apparatus according to claim 17, wherein the second function denotes a correlation between the feature values of the second material and measurement errors of the first material.

20. The error correction apparatus according to claim 17, wherein the first material is glucose in blood, and the second material is a red blood cell in blood.

\* \* \* \* \*